(12) United States Patent
Liu et al.

(10) Patent No.: US 9,434,967 B2
(45) Date of Patent: Sep. 6, 2016

(54) MICROBIAL CULTURE MEDIUM AND CULTURAL METHOD

(71) Applicant: ENN Science and Technology Development Co., Ltd., LangFang (CN)

(72) Inventors: Minsheng Liu, LangFang (CN); Qian Feng, LangFang (CN); Zhongzhen Cai, LangFang (CN); Lin Wang, LangFang (CN)

(73) Assignee: ENN SCIENCE AND TECHNOLOGY DEVELOPMENT CO., LTD., Langfang (CN)

( * ) Notice: Subject to any disclaimer, the term of this patent is extended or adjusted under 35 U.S.C. 154(b) by 121 days.

(21) Appl. No.: 14/041,473

(22) Filed: Sep. 30, 2013

(65) Prior Publication Data

US 2014/0093922 A1    Apr. 3, 2014

(30) Foreign Application Priority Data

Sep. 28, 2012 (CN) .......................... 2012 1 0369787

(51) Int. Cl.
   *C12P 7/64*   (2006.01)
   *C12N 1/12*   (2006.01)
(52) U.S. Cl.
   CPC ............... *C12P 7/6427* (2013.01); *C12N 1/12* (2013.01)
(58) Field of Classification Search
   None
   See application file for complete search history.

(56) References Cited

FOREIGN PATENT DOCUMENTS

| CN | 1218035 C | 9/2005 | | |
|----|-----------|--------|---|---|
| CN | 1914327 A | 2/2007 | | |
| CN | 101037658 A | 9/2007 | | |
| CN | 101812484 A | 8/2010 | | |
| CN | 101591617 B | 3/2011 | | |
| CN | 101519676 B | 9/2011 | | |
| CN | 101528939 B | 5/2012 | | |
| CN | 101538592 B | 6/2012 | | |
| IL | WO 2010/113149 | * | 10/2010 | ............... C12N 1/13 |
| JP | EP 1041154 | * | 10/2000 | ............... C12P 13/00 |

OTHER PUBLICATIONS

Chinese Patent Office; Office Action for Chinese Application No. 201210369787.X dated Nov. 5, 2014, 9 Pages.

* cited by examiner

*Primary Examiner* — Karen Cochrane Carlson
*Assistant Examiner* — Jennifer M. H. Tichy
(74) *Attorney, Agent, or Firm* — Moore & Van Allen PLLC

(57) ABSTRACT

The present invention discloses a microbial culture medium and a cultural method. The culture medium comprises a combination of strong acid-weak alkali salts and strong alkali-weak acid salts so that pH value thereof can be regulated and controlled in a stable and suitable range by itself, thus decreasing or eliminating an operable regulation on pH value via an external device in fermentation process and a risk of contaminations resulted from it in fermentation process as well, accordingly greatly improving the controllability and stability of the fermentation process. Meanwhile the ammonium salts acting as strong acid-weak alkali salts can be used as a nitrogen source to replace yeast cream to realize a decreased amount of nitrogen resource of high price, therefor sharply reducing the cost of the culture medium.

5 Claims, 1 Drawing Sheet

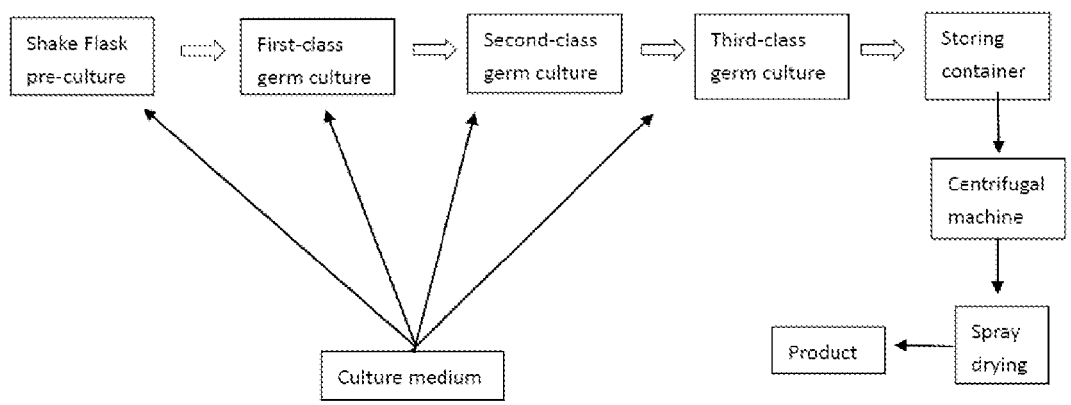

MICROBIAL CULTURE MEDIUM AND CULTURAL METHOD

TECHNICAL FIELD

The present invention relates to the microbiology and particularly relates to a microbial culture medium and a cultural method using it.

BACKGROUND OF THE INVENTION

Polyunsaturated fatty acids (PUFA) refers to a strait chain fatty acid having two or more double bonds and a carbon chain with a length of 16-22 carbon atoms, which are important components of cell membranes and biofilms in an organism and able to regulate cell configuration, dynamic equilibrium and maintain cell membrane relative liquidity, thereby maintaining normal physiological functions of a cell. Therefor they can influence cell chemical composition and functions such as signal transmission, immunity and the like, and thus have great contribution to occurrences of relative disease. PUFA possesses important physiological regulation functions in human body, comprising esterifying cholesterol, reducing cholesterol and triglyceride in blood, reducing blood viscosity, improving blood microcirculation, increasing activity of brain cells and enhancing memory and intelligence, etc. PUFA includes eicosapentaenoic acid (EPA), docosahexaenoic acid (DHA) and the like, wherein DHA can prevent and treat cardiovascular disease, improve blood viscosity and increase deformability of erythrocytes, prevent and treat cancer, reduce thrombus and inflammation. Also, DHA is an main component of human brain, playing an important role in normal brain growth of infants and on normal functioning of adult brains. Some research suggests that the lack of DHA leads to decrease brain function, so, experts recommend that adults and pregnant women should supply with PUFA-rich food, such as marine fish for moderate supplement. DHA is a commendable component for medicines and nutrients.

Considering the important functions and effects of PUFA, it is widely focused in medicine and food fields. The conventional preparation of PUFA is separating from fish oil. However, the PUFA separated from fish oil has a strong fishy taste, a limited source and an unstable yield. The amount of W-3 unsaturated fatty acid in fish oil varies depending on fish spices as well as fishing seasons, weather and locations, and the production of fish oil has fluctuated output and involves complicated purification processes and the product yield is low. Meanwhile, the occurrence of reckless overfishing for the commercial profits, because of the big demand, brings bad effects on environmental resource protection. Therefore, the conventional preparation of fish oil cannot meet the needs.

Currently, it has been found that microorganism can be used for producing PUFA and plenty of research on it has been done. Particularly the method for producing PUFA such as DHA and the like by fermentation of algae has been the current research focus. This method goes beyond the limitation of conditions such as season, location and the like, obtains fatty acid with high content and simple component, greatly simplifies the purification process, decreases the difficulty of refining, and the culture condition thereof is easier to control, which provides the possibility of controlling the amount and constituent of lipid. Producing PUFA such as DHA by fermentation of microorganism also can reduce the negative effect on environmental resource caused by excessively fishing because of market demand.

The method for producing PUFA by fermentation of microorganism can realize the operable control of temperature, dissolved oxygen, pH value, thereby easier to realize culture process and the controllability and stability of products. Due to the appearance of metabolic products and/or the consumption of some component in the medium, the common problem during the fermentation is a drastic undulation of pH value. In this condition, if pH value is not suitably regulated during the fermentation of microorganism, the metabolic rate and cell growth will be impacted, and even the cell growth stops. Accordingly, a regulation of pH value is needed in fermentation of microorganism.

In the prior art, the conventional method for pH value regulation during the process for producing PUFA by fermentation of microorganism is to supply an acid-base solution to the fermentation system with an external device. Although this method can control pH value in a stable range to some degree, there still exists come problems, such as extra devices, sterilization process and labor costs, and more worse, an increased risk of microorganism contaminations during the fermentation process, for once there occurs microorganism contamination during the fermentation, it will have a dramatic effect on stable production and cause a great economic loss.

Beside the use of an external device, in recent years, adjusting the constituent of culture medium so that pH value thereof can be regulated by itself also is a research area and an effective mean to regulate pH value during the fermentation process, comprising:

(1) Adding strong alkali-weak acid salts to medium. CN101538592B discloses a method for producing docosahexaenoic by industrial *Crypthecodinium cohnii* fermentation, wherein sodium glutamate is added to the medium thereby omitting a pH value regulation during fermentation; CN101519676B discloses a method for producing docosahexaenoic by industrial *Crypthecodinium cohnii* fermentation, wherein sodium glutamate is added to the medium and citric acid is supplied to the system during fermentation; CN1218035C discloses a method for producing long chain PUFA with heterotrophic culture of marine microalgae, wherein sodium glutamate is added to the medium thereby omitting a pH value regulation during fermentation; CN101591617B discloses a strain producing docosahexaenoic and the mutation screening and use thereof, wherein sodium glutamate and sodium bicarbonate are added to the medium thereby omitting a pH value regulation during fermentation. In these methods comprising supplying strong alkali-weak acid salts for example sodium glutamate as nitrogen source in the medium, the pH value has a notable increase during the fermentation process as strong alkali-weak acid salts are consumed by the cell. As excessively high pH value will severely affect and change the metabolic process in cell, thus causing a decreased yield in fermentation process. However, when an external device is needed to supply the acid solution for pH value regulation, it not only increases the equipment investment, but also takes a risk of contaminations.

(2) Adding strong acid weak alkali salts such as inorganic ammonium salts to medium. CN101528939B discloses using an improved medium to produce ω-3 fatty acid from the *Thraustochytriales*, wherein sodium hydroxide is supplied during fermentation for pH value regulation; CN101812484B discloses a method for producing DHA via fermentation by high density *Schizochytrium* culture wherein ammonium hydroxide is supplied to the system for pH value regulation. A series of inventions by Richard B. Bailey et al respectively disclose methods for increasing the generation of lipid containing polyenoid fatty acids by high density eukaryotic microorganism culture in a fermentor and ammonium hydroxide is supplied in fermentation process for pH value regulation. In these methods comprising supplying strong acid-weak alkali salts like inorganic ammonium salts as nitrogen source in the medium, the pH value has a notable decrease during the fermentation process as strong acid-weak alkali salts are consumed. Excessively low pH value results in rancidity in fermentation system, which will severely affect and change the metabolic process in cell, thus causing a decreased yield in fermentation process. Meanwhile strong acid circumstance does seriously harm to fermentation devices, which makes it unsuitable to constantly and stably produce unsaturated fatty acids with microorganism. If supplying a base solution or other one with high pH value for pH value regulation, it not only increases the equipment investment, but also takes a risk of contaminations.

In addition, CN1914327A discloses a method for *THRAUSTOCHYTRIALES* microorganism culture, which regulates and stabilizes pH value in fermentation process by adding calcium carbonate to the medium. Due to limited solubility in water carbon dioxide generated from calcium carbonate during fermentation process, however, the buffer capacity of the buffer system decreases during fermentation process.

Accordingly a novel solution to medium is required to realize highly effective and stable control on the pH value during fermentation process in the art.

SUMMARY OF THE INVENTION

The present invention provides a solution to microorganism medium, for eliminating the impact on cell growth from up and down fluctuations of pH value in fermentation process, decreasing or eliminating a conventional acid-base operation via an external device in fermentation process and a risk of contaminations resulted from it as well. The solution to microorganism medium controls the pH value in a stable range by a combination of nutrient substances to realize a simple but highly effective control on pH value in fermentation process, which is of great significance to large-scale production of unsaturated fatty acids generated by microorganism fermentation.

For this object, the present invention adopts the following technical solutions:

In one aspect, the present invention provides a culture medium, comprising a combination of strong acid-weak alkali salts and strong alkali-weak acid salts to control the pH value in fermentation process, wherein said strong acid-weak alkali salts are organic or inorganic strong acid ammonium salts, preferably ammonium nitrate, ammonium sulfate, ammonium chloride and ammonium oxalate, more preferably ammonium sulfate; said strong alkali-weak acid salts is sodium, potassium or calcium salts of carbonic acid or amino acid.

In the culture medium of the present invention, said combination of strong acid-weak alkali salts and strong alkali-weak acid salts can be used to control the pH value of the medium in range from 4.0 to 9.0, preferably from 5.0 to 8.0, the most preferably from 6.0 to 7.0.

In the culture medium of the present invention, the sodium, potassium or calcium salts of amino acid may be sodium, potassium or calcium salt of glutamic acid, aspartic acid, lysine, arginine, histidine, glycine, serine, threonine, cysteine, tyrosine, alanine, valine, leucine, isoleucine, auxiliary leucine, phenylalanine, tryptophan, methionine or a mixture of at least two thereof.

In the culture medium of the present invention, said strong alkali-weak acid salts may be sodium glutamate.

In the culture medium of the present invention, the amount of sodium glutamate may be from 1 to 20 g/L, preferably from 5 to 15 g/L, more preferably from 8 to 12 g/L, the most preferably 10 g/L.

In the culture medium of the present invention, the amount of ammonium sulfate may be from 0.5 to 5 g/L, preferably from 1 to 4 g/L, more preferably from 2 to 3.5 g/L, the most preferably 3 g/L.

The culture medium of the present invention may further contain other nitrogen sources, carbon sources, inorganic salts and microelements.

Preferably, said carbon sources are molasses, sugarcane juice, corn flour, sucrose, fructose, glucose, soluble starch, carbon dioxide or a mixture of at least two thereof.

Preferably, said nitrogen sources are organic nitrogen compounds, inorganic nitrogen compounds or a mixture thereof.

Preferably, said inorganic salts include sodium, magnesium, potassium, iron, calcium, sulfate, carbonate, bicarbonate, acetate salts or a mixture of at least two thereof; and/or Preferably, said microelement include vitamin B1, vitamin B6, vitamin B12, vitamin H, 6-benzyl amino adenine (6-BA) or a mixture of at least two thereof.

In the culture medium of the present invention, said organic nitrogen compounds include yeast extract, yeast cream, corn steep liquor, peptone, amino acids, sodium glutamate or a mixture of at least two thereof.

In the culture medium of the present invention, said inorganic nitrogen compounds include urea, nitrites, nitrates, inorganic ammonium salts or a mixture of least two thereof.

The culture medium of the present invention may include: 10 to 200 g/L of glucose, 1 to 20 g/L of sodium glutamate, 0.5 to 5 g/L of ammonium sulfate, yeast cream at concentration as ½ to ¹⁄₁₀ of carbon source, preferably 5 to 20 g/L, 0.1 to 35 g/L of said inorganic salts based on sodium salts, and as said microelements, 10 to 30 ppm of vitamin B1, 5 to 15 ppm of vitamin B6, 1 to 5 ppm of vitamin B12, 1 to 5 ppm of vitamin H, 3 to 15 ppm of 6-BA.

The pH value in the culture medium of the present invention may be 4.0, 4.5, 5.0, 5.5, 6.0, 6.5, 7.0, 7.5, 8.0, 8.5 or 9.0.

The amount of sodium glutamate in the culture medium of the present invention may be 1 g/L, 2 g/L, 3 g/L, 4 g/L, 5 g/L, 6 g/L, 7 g/L, 8 g/L, 9 g/L, 10 g/L, 11 g/L, 12 g/L, 13 g/L, 14 g/L, 15 g/L, 16 g/L, 17 g/L, 18 g/L, 19 g/L, or 20 g/L.

The amount of sodium sulfate in the culture medium of the present invention may be 0.5 g/L, 1.0 g/L, 1.5 g/L, 2.0 g/L, 2.5 g/L, 3.0 g/L, 3.5 g/L, 4.0 g/L, 4.5 g/L or 5.0 g/L.

The amount of glucose in the culture medium of the present invention may be 10 g/L, 20 g/L, 30 g/L, 40 g/L, 50 g/L, 60 g/L, 70 g/L, 80 g/L, 90 g/L, 100 g/L, 110 g/L, 120 g/L, 130 g/L, 140 g/L, 150 g/L, 160 g/L, 170 g/L, 180 g/L, 190 g/L or 200 g/L.

The amount of yeast cream in the culture medium of the present invention may be 1 g/L, 5 g/L, 10 g/L, 15 g/L, 20 g/L, 25 g/L, 30 g/L, 35 g/L, 40 g/L, 45 g/L, 50 g/L, 55 g/L, 60 g/L, 65 g/L, 70 g/L, 75 g/L, 80 g/L, 85 g/L, 90 g/L, 95 g/L or 100 g/L.

The amount of inorganic salts in the culture medium of the present invention (based on sodium salts) may be 0.1 g/L, 0.5 g/L, 1 g/L, 5 g/L, 10 g/L, 15 g/L, 20 g/L, 25 g/L, 30 g/L or 35 g/L.

The concentration of vitamin B1 in the culture medium of the present invention may be 10 ppm, 15 ppm, 20 ppm, 25 ppm or 30 ppm.

The concentration of vitamin B6 in the culture medium of the present invention may be 5 ppm, 8 ppm, 10 ppm, 12 ppm or 15 ppm.

The concentration of vitamin B12 in the culture medium of the present invention may be 1 ppm, 2 ppm, 3 ppm, 4 ppm or 5 ppm.

The concentration of vitamin H in the culture medium of the present invention may be 1 ppm, 2 ppm, 3 ppm, 4 ppm or 5 ppm.

The concentration of 6-BA in the culture medium of the present invention may be 3 ppm, 6 ppm, 9 ppm, 12 ppm or 15 ppm.

In another aspect, the present invention provides a method for microorganism culture, comprising using the culture medium described in the first aspect in fermentation process.

In the method of the present invention, said microorganism may be microalgae.

The method of the present invention may comprise shake flask pre-culture, first-stage germ culture, second-stage germ culture and/or third stage fermentation culture using the culture medium as described above.

The culture method of the present invention includes:

a) activated culture. Algae were isolated by plate or slant streaking, cultured in a constant temperature at 25° C. for 3 to 5 days and then algae colonies with good morphology and growth was selected and isolated by plate or slant streak again and then cultured in a constant temperature at 25° C. for 3 to 5 days.

b) Shake flask pre-culture. A activated algae colony was picked and inoculated to a clean shake flask and then shake cultured at 25° C., at 150 to 300 rpm, preferably 150 to 150 rpm, the most preferably 200 rpm.

c) Fermentation scale-up culture. wherein first-stage germ culture comprises inoculating the algae obtained in shake flask pre-culture to a first-stage germ container with an inoculated amount of 2% to 10%, preferably 4% to 8%, the most preferably 6%, aerating sterilized air at 0.4 to 1.0 vvm, preferably 0.5 to 0.8 vvm, the most preferably 0.7 vvm, stirring at a rate of 100 to 300 rpm, preferably 150 to 250 rpm, the most preferably 200 rpm, and controlling the culture temperature in range from 24 to 28° C., preferably 25 to 27° C., the most preferably 26° C.; second-stage germ culture comprises inoculating the fermentation germ solution in the first-stage germ container to a second-stage germ container with an inoculated amount of 5% to 15%, preferably 7% to 13%, the most preferably 10%; aerating sterilized air at 0.4 to 1.0 vvm, preferably 0.5 to 0.8 vvm, the most preferably 0.7 vvm, stirring at a rate of 100 to 300 rpm, preferably 150 to 250 rpm, the most preferably 200 rpm and controlling the culture temperature in range from 24 to 28° C., preferably 25 to 27° C., the most preferably 25° C.; fermentation culture comprises inoculating the fermentation germ solution in the second-stage germ container to a third-stage fermentation container with an inoculated amount of 7% to 13%, the most preferably 10%; aerating sterilized air at 0.4 to 1.0 vvm, preferably 0.5 to 0.8 vvm, the most preferably 0.7 vvm was blew, stirring at a rate of 100 to 200 rpm, preferably 120 to 180 rpm, the most preferably 150 rpm and controlling the culture temperature in range from 24 to 28° C., preferably 25 to 27° C., the most preferably 26° C.

Wherein the culture medium used in b) and c) is both the culture medium of the present invention as described above.

Advantage Effect (1) The present invention realizes a highly effective control on fluctuations of pH value in fermentation process via designing the constituents of the fermentation culture medium, thereby controlling the pH value to a stable and suitable range, and decreasing or eliminating an acid-base operation though supplying acids or alkali via an external device in fermentation process as well as a risk of contaminations resulted from it, thus greatly improving the controllability and stability of the fermentation process.

(2) The ammonium salts used in the method of the present invention may be used as a nitrogen source to replace yeast cream to realize a decreased amount of nitrogen resource of high price, therefor sharply reducing the cost of the culture medium.

DESCRIPTION OF THE DRAWING

FIG. 1 is a process schematic diagram of the culture method of the present invention.

DESCRIPTION OF THE PREFERRED EMBODIMENTS

Example 1

A three stages scale-up algae culture of 500 L, 6 cubic meters, and 60 cubic meters is proceeded according to the following steps with the culture medium of the present invention (the specific constituents are shown in table 1), wherein said algae belongs to *Thraustochytrids* species.

Firstly, algae were activated. Algae were isolated by plate or slant streaking, cultured in a constant temperature at 25° C. for 3 to 5 days and then algae colonies with good morphology and growth were selected and isolated by plate or slant streak again and then cultured in a constant temperature at 25° C. for 3 to 5 days and then cryopreserved as the algae strain for shake flask pre-culture.

Secondly, shake flask pre-culture is proceeded. The activated algae colony was selected and inoculated to a clean shake flask comprising aforesaid culture medium and then shake cultured at 25° C. at 150 to 300 rpm. This step may include second-third stage scale-up pre-culture. The shake flask germs were combined to a sterilized container after the germ pre-culture. This step is germ pre-culture process.

Thirdly the fermentation sale-up culture is proceeded, comprising first, second, third-stage fermentation sale-up culture, particularly comprising first-stage germ culture: inoculating the shake flask germ to a first-stage germ container via a flame inoculation method or a differential pressure inoculation method with an inoculated amount of 2% to 10%, aerating sterilized air at 0.4 to 1.0 vvm, stirring at a rate of 100 to 300 rpm and controlling the culture temperature in the range of 24° C. to 28° C., the most preferably 26° C.; second-stage germ culture: inoculating the fermentation germ solution in the first-stage germ container at certain stage of the first-stage germ culture to a second-stage germ container comprising aforesaid culture medium via a flame inoculation method or a differential pressure inoculation method with an inoculated amount of 5% to 15%, aerating sterilized air at 0.4 to 1.0 vvm, stirring at a rate of 100 to 300 rpm and controlling the culture temperature in the range of 24° C. to 28° C., the most preferably 25° C.; fermentation culture: inoculating the fermentation germ solution in the second-stage germ container at a certain stage of the second-stage germ culture to a third-stage germ container comprising aforesaid culture medium via a flame inoculation method or a differential pressure inoculation method with an inoculated amount of 5% to 15%, aerating sterilized air at 0.4 to 1.0 vvm, stirring at a rate of 100 to 300 rpm and controlling the culture temperature in the range of 24° C. to 28° C., the most preferably 25° C. to proceed a fermentation culture.

Finally, when the dry cell weight increases to a platform or the when the cell is unsuitable to continue culture, fermentation culture is halted and the fermentation solution is stored in a storing container. The fermentation solution is concentrated by a centrifugal machine and dried in a spray drying tower to obtain the product.

The consumption of two salts causes up and down fluctuations of pH value in fermentation process. As the impacts from the two salts can counteract with each other, stable and highly effective control of pH value in fermentation process is realized.

TABLE 1

Components of the culture medium

| Component | Amount (g/L) | Component | Amount (g/L) |
|---|---|---|---|
| Glucose | 30 | Vitamin B1 | 30 |
| Yeast cream | 15 | Vitamin B6 | 5 |
| Sodium glutamate | 1 | Vitamin B12 | 1 |
| Ammonia nitrate | 0.5 | Vitamin H | 1 |
| Sodium chloride | 12 | 6-BA | 3 |
| Magnesium sulphate | 3 | | |
| Magnesium chloride | 3 | | |
| Potassium chloride | 1 | | |
| Calcium sulphate | 1 | | |

In fermentation process, dry cell weight, glucose concentration, pH value and nitrogen concentration in ammonium were detected and nutrients like nitrogen and carbon sources were supplied according to cell growth. 50% glucose solution was added to reach a glucose concentration of 1.5 to 2% in the fermentation solution when the concentration of carbon source was less than 1%. Therefor there is no need for an external device to supply extra acid-base solution for pH value regulation. As a result, the pH value in the medium is stabilized substantially in the range of 5.0 to 7.0, which is suitable for algae culture.

Example 2

A three stages scale-up algae culture of 500 L, 6 cubic meters, and 60 cubic meters is proceeded with the same algae and method as example 1 and the culture medium (the specific constituents are shown in table 2) of the present invention.

TABLE 2

Components of the culture medium

| Component | Amount (g/L) | Component | Amount (g/L) |
|---|---|---|---|
| Glucose | 80 | Vitamin B1 | 10 |
| Yeast cream | 30 | Vitamin B6 | 15 |
| Sodium glutamate | 15 | Vitamin B12 | 5 |
| Ammonia nitrate | 4 | Vitamin H | 5 |
| Sodium chloride | 5 | 6-BA | 3 |
| Magnesium sulphate | 1 | | |
| Magnesium chloride | 1 | | |
| Potassium chloride | 1 | | |
| Calcium sulphate | 1 | | |

Similar to example 1, in fermentation process, dry cell weight, glucose concentration, pH value and nitrogen concentration in ammonium were detected and nutrients like nitrogen and carbon sources were supplied according to cell growth. As a result, the pH value in the medium is stabilized substantially in the range of 5.5 to 6.8, which is suitable for algae culture.

Example 3

A three stages scale-up algae culture of 500 L, 6 cubic meters, and 60 cubic meters is proceeded with the same algae and method as example 1 and the culture medium (the specific constituents are shown in table 3) of the present invention.

TABLE 3

Components of the culture medium

| Component | Amount (g/L) | Component | Amount (g/L) |
|---|---|---|---|
| Glucose | 100 | Vitamin B1 | 10 |
| Yeast cream | 40 | Vitamin B6 | 15 |
| Sodium glutamate | 20 | Vitamin B12 | 5 |
| Ammonia nitrate | 3 | Vitamin H | 5 |
| Sodium chloride | 5 | 6-BA | 3 |
| Magnesium sulphate | 1 | | |
| Magnesium chloride | 1 | | |
| Potassium chloride | 0.5 | | |
| Calcium sulphate | 0.1 | | |

Similar to example 1, in fermentation process, dry cell weight, glucose concentration, pH value and nitrogen concentration in ammonium were detected and nutrients like nitrogen and carbon sources were supplied according to cell growth. As a result, the pH value in the medium is stabilized substantially in the range of 4.5 to 6.0, which is suitable for algae culture.

Example 4

A three stages scale-up algae culture of 500 L, 6 cubic meters, and 60 cubic meters is proceeded with the same algae and method as example 1 and the culture medium (the specific constituents are shown in table 4) of the present invention.

TABLE 4

Components of the culture medium

| Component | Amount (g/L) | Component | Amount (g/L) |
|---|---|---|---|
| Glucose | 200 | Vitamin B1 | 10 |
| Yeast cream | 100 | Vitamin B6 | 15 |

TABLE 4-continued

Components of the culture medium

| Component | Amount (g/L) | Component | Amount (g/L) |
|---|---|---|---|
| Sodium glutamate | 20 | Vitamin B12 | 5 |
| Ammonia nitrate | 5 | Vitamin H | 5 |
| Sodium chloride | 12 | 6-BA | 3 |
| Magnesium sulphate | 1 | | |
| Magnesium chloride | 1 | | |
| Potassium chloride | 1 | | |
| Calcium sulphate | 1 | | |

Similar to example 1, in fermentation process, dry cell weight, glucose concentration, pH value and nitrogen concentration in ammonium were detected and nutrients like nitrogen and carbon sources were supplied according to cell growth. As a result, the pH value in the medium is stabilized substantially in the range of 5.3 to 6.5, which is suitable for algae culture.

Example 5

A three stages scale-up algae culture of 500 L, 6 cubic meters, and 60 cubic meters is proceeded with the algae of *Scenedesmus* species and the culture medium (the specific constituents are shown in table 5) of the present invention.

TABLE 5

Components of the culture medium

| Component | Amount (g/L) | Component | Amount (g/L) |
|---|---|---|---|
| Glucose | 60 | Vitamin B1 | 20 |
| Yeast cream | 20 | Vitamin B6 | 15 |
| Sodium glutamate | 10 | Vitamin B12 | 5 |
| Ammonia nitrate | 3.5 | Vitamin H | 5 |
| Sodium chloride | 5 | 6-BA | 3 |
| Magnesium sulphate | 1 | | |
| Magnesium chloride | 1 | | |
| Potassium chloride | 1 | | |
| Calcium sulphate | 1 | | |

Similar to example 1, in fermentation process, dry cell weight, glucose concentration, pH value and nitrogen concentration in ammonium were detected and nutrients like nitrogen and carbon sources were supplied according to cell growth. As a result, the pH value in the medium is stabilized substantially in the range of 6.5 to 8.2, which is suitable for algae culture.

Example 6

A three stages scale-up algae culture of 500 L, 6 cubic meters, and 60 cubic meters is proceeded with the same algae as example 5 and the culture medium (the specific constituents are shown in table 6) of the present invention.

TABLE 6

Components of the culture medium

| Component | Amount (g/L) | Component | Amount (g/L) |
|---|---|---|---|
| Glucose | 150 | Vitamin B1 | 20 |
| Yeast cream | 70 | Vitamin B6 | 15 |

TABLE 6-continued

Components of the culture medium

| Component | Amount (g/L) | Component | Amount (g/L) |
|---|---|---|---|
| Sodium glutamate | 5 | Vitamin B12 | 5 |
| Ammonia nitrate | 4.5 | Vitamin H | 5 |
| Sodium chloride | 5 | 6-BA | 3 |
| Magnesium sulphate | 1 | | |
| Magnesium chloride | 1 | | |
| Potassium chloride | 1 | | |
| Calcium sulphate | 1 | | |

Similar to example 1, in fermentation process, dry cell weight, glucose concentration, pH value and nitrogen concentration in ammonium were detected and nutrients like nitrogen and carbon sources were supplied according to cell growth. As a result, the pH value in the medium is stabilized substantially in the range of 7.8 to 9.0, which is suitable for algae culture.

Example 7

A three stages scale-up algae culture of 500 L, 6 cubic meters, and 60 cubic meters is proceeded with the same algae as example 5 and the culture medium (the specific constituents are shown in table 7) of the present invention.

TABLE 7

Components of the culture medium

| Component | Amount (g/L) | Component | Amount (g/L) |
|---|---|---|---|
| Glucose | 10 | Vitamin B1 | 20 |
| Yeast cream | 5 | Vitamin B6 | 15 |
| Sodium glutamate | 10 | Vitamin B12 | 5 |
| Ammonia nitrate | 3.5 | Vitamin H | 5 |
| Sodium chloride | 5 | 6-BA | 3 |
| Magnesium sulphate | 1 | | |
| Magnesium chloride | 1 | | |
| Potassium chloride | 1 | | |
| Calcium sulphate | 1 | | |

Similar to example 1, in fermentation process, dry cell weight, glucose concentration, pH value and nitrogen concentration in ammonium were detected and nutrients like nitrogen and carbon sources were supplied according to cell growth. As a result, the pH value in the medium is stabilized substantially in the range of 6.8 to 8.3, which is suitable for algae culture.

The examples used above are for the purpose of describing particular characteristics and method, and is not to be understood that the present invention is realized via particular characteristics and method above only. And it is also to be understood by those skilled in the art that any improvement, addition or equivalent replacement in the constituent selected by present invention and the selection of embodiment all fall within the scope protected and disclosed by present invention.

The invention claimed is:
1. A fermentation medium for algae comprising
a combination of strong acid-weak alkali salts and strong alkali-weak acid salts, wherein said strong acid-weak alkali salts are selected from ammonium nitrate, ammonium sulfate, ammonium chloride and ammonium oxalate or a mixture of at least two thereof in an amount of 3 to 5 g/L; and said strong alkali-weak acid salts are sodium, potassium or calcium salts of glutamic acid, aspartic acid, lysine, arginine, histidine, glycine, serine, threonine, cysteine, tyrosine, alanine, valine, leucine, isoleucine, auxiliary leucine, phenylalanine, tryptophan, methionine or a mixture of at least two thereof in an amount of 5 to 20 g/L, and further comprising 10 to 200 g/L of glucose, 5 to 20 g/L of yeast cream, 0.1 to 35 g/L of inorganic salts, 10 to 30 ppm of vitamin B1, 5 to 15 ppm of vitamin B6, 1 to 5 ppm of vitamin B 12, 1 to 5 ppm of vitamin H, and 3 to 15 ppm of 6-benzyl amino adenine.

2. The medium of claim 1, characterized in that said combination of strong acid-weak alkali salts and strong alkali-weak acid salts controls the pH value of the medium in range from 4.0 to 9.0.

3. The medium of claim 1, characterized in that said strong alkali-weak acid salt is sodium glutamate.

4. The medium of claim 1, further comprising: 5 to 20 g/L of sodium glutamate, and 3.5 to 5 g/L of ammonium sulfate.

5. The culture medium of claim 1, characterized in that said combination of strong acid-weak alkali salts and strong alkali-weak acid salts controls the pH value of the medium in range from 4.5 to 6.0.

* * * * *